US011065368B2

(12) United States Patent
Peck et al.

(10) Patent No.: US 11,065,368 B2
(45) Date of Patent: Jul. 20, 2021

(54) DRUG ELUTING GRAFT CONSTRUCTS AND METHODS

(71) Applicants: Cook Medical Technologies LLC, Bloomington, IN (US); Cook Biotech Incorporated, West Lafayette, IN (US)

(72) Inventors: Rhonda Peck, West Lafayette, IN (US); Bhavin Shah, West Lafayette, IN (US); Umesh H. Patel, West Lafayette, IN (US); Krista Gearhart, Lafayette, IN (US); Steven Charlebois, West Lafayette, IN (US); Keith Milner, West Lafayette, IN (US); Eric J. Rodenberg, Battle Ground, IN (US)

(73) Assignees: Cook Biotech Incorporated, West Lafayette, IN (US); Cook Medical Technologies LLC, Bloomington, IN (US)

(*) Notice: Subject to any disclaimer, the term of this patent is extended or adjusted under 35 U.S.C. 154(b) by 242 days.

(21) Appl. No.: 14/210,903

(22) Filed: Mar. 14, 2014

(65) Prior Publication Data
US 2014/0315847 A1    Oct. 23, 2014

Related U.S. Application Data

(60) Provisional application No. 61/799,080, filed on Mar. 15, 2013.

(51) Int. Cl.
| A61L 31/14 | (2006.01) |
| A61L 31/16 | (2006.01) |
| A61L 31/00 | (2006.01) |
| A61L 27/56 | (2006.01) |
| A61L 27/54 | (2006.01) |
| A61L 27/36 | (2006.01) |

(52) U.S. Cl.
CPC ......... A61L 31/146 (2013.01); A61L 27/3633 (2013.01); A61L 27/54 (2013.01); A61L 27/56 (2013.01); A61L 31/005 (2013.01); A61L 31/16 (2013.01); A61L 2300/406 (2013.01); A61L 2300/414 (2013.01)

(58) Field of Classification Search
CPC ... A61L 31/146; A61L 2300/406; A61L 31/16
See application file for complete search history.

(56) References Cited

U.S. PATENT DOCUMENTS

| 6,096,070 | A | 8/2000 | Ragheb et al. |
| 6,206,931 | B1 | 3/2001 | Cook et al. |
| 7,056,338 | B2* | 6/2006 | Shanley et al. ............... 623/1.42 |
| 8,268,340 | B2 | 9/2012 | Choubey et al. |
| 2003/0023190 | A1* | 1/2003 | Cox ............................... 600/585 |
| 2006/0251702 | A1 | 11/2006 | Janis et al. |
| 2007/0134292 | A1 | 6/2007 | Suokas et al. |
| 2009/0005867 | A1* | 1/2009 | Lefranc ................. A61F 2/0045 623/11.11 |
| 2009/0149947 | A1* | 6/2009 | Frohwitter ................... 623/1.42 |
| 2009/0306688 | A1 | 12/2009 | Patel et al. |
| 2009/0311298 | A1* | 12/2009 | Nixon et al. .................. 424/423 |
| 2011/0098724 | A1 | 4/2011 | Cichocki et al. |
| 2012/0135045 | A1 | 5/2012 | Nixon et al. |

FOREIGN PATENT DOCUMENTS

| EP | 1 604 697 A1 | 12/2005 |
| WO | WO 2004/103212 A1 | 12/2004 |
| WO | WO 2005/097219 A2 | 10/2005 |
| WO | WO 2012/116182 | 8/2012 |

OTHER PUBLICATIONS

Lodish, H et al., Collagen: The Fibrious Proteins of the Matrix, (2000), pp. 1-5.*
International Search Report and Written Opinion issued in PCT/US2014/028488, dated Jul. 10, 2014, 13 pgs.

* cited by examiner

*Primary Examiner* — Andrew S Rosenthal
*Assistant Examiner* — Lyndsey M Beckhardt
(74) *Attorney, Agent, or Firm* — Woodard Emhardt Henry Reeves & Wagner LLP

(57) ABSTRACT

The present invention provides, in certain aspects, medical graft products that incorporate multiple drug depots in and/or on the products. One such product is a sheet graft construct, for example for tissue support that includes a sheet graft material with a plurality of drug depots. The drug depots can be hardened deposits formed directly onto the sheet graft material and/or can be capable of eluting a drug for a minimum of 72 hours.

22 Claims, 8 Drawing Sheets

DRUG ELUTING GRAFT CONSTRUCTS AND METHODS

CROSS-REFERENCE TO RELATED APPLICATIONS

This application claims the benefit of U.S. Provisional Application Ser. No. 61/799,080, filed on Mar. 15, 2013, which is incorporated herein by reference in its entirety.

BACKGROUND

The present invention relates generally to medical technology and in particular aspects to medical graft constructs with the capacity to elute a drug.

As further background, a variety of materials have been used to form implants, grafts and other medical constructs. These materials include both naturally derived and non-naturally derived materials. In some cases, bioremodelable materials including remodelable extracellular matrix (ECM) materials have been used. Remodelable ECM materials can be provided, for example, by materials isolated from a suitable tissue source from a warm-blooded vertebrate, e.g., from the submucosal, dermal or other tissue of a mammal. Such isolated tissue, for example, small intestinal submucosa (SIS), can be processed so as to have bioremodelable properties and promote cellular invasion and ingrowth. Illustratively, sheet-form SIS material has been suggested and used to form hernia repair grafts and other medical products. Some of these grafts exhibit a multiple layer configuration to provide strength and/or reinforcement.

There remain needs for improved and/or alternative medical materials and constructs, as well as methods for preparing and utilizing the same. The present invention is addressed to those needs.

SUMMARY

The present invention provides, in certain aspects, products that include drug depots carried by a sheet material. The drug depots can, in embodiments herein, include a limited number of depots that incorporate a substantial percentage, for example at least 50% by weight, of the total dose of the drug applied to the product.

In certain embodiments, provided is an implantable device that includes a sheet graft material having a top side and a bottom side, and a plurality of drug depots attached to the sheet graft material. The sheet graft material can include an extracellular matrix sheet material, and/or can have a porous matrix formed by a network of fibers, the porous matrix having pores formed between the fibers of the network. The drug depots can comprise solid deposits including a polymeric carrier and a drug. When the sheet graft material has a porous matrix, such solid deposits can include a first portion infiltrating pores of the porous matrix and a second portion external of the porous matrix, and/or the porous matrix can facilitate the distribution of the drug into depot-free regions of the graft material by diffusion of dissolved, eluted amounts of the drug through the porous matrix. The drug can be an antibiotic agent, for example gentamycin. The drug depots can be constructed and arranged so as to have the capacity to elute the drug over a time period of at least about 72 hours, or at least about 96 hours, when the implantable device is immersed in an aqueous medium such as an aqueous phosphate buffered saline (PBS) solution at 37° C. The PBS can be a 66.7 mM phosphate buffer saline solution, prepared for example as described in Example 1 below. The implantable device can incorporate at least 50%, at least 70%, at least 80%, at least 90%, or essentially all (at least 99%), of the total dose of the drug on the device within 2 to about 120 depots attached to the sheet graft material, preferably about 5 to about 80 depots, and more preferably about 10 to about 60 depots. These specified depots can each be constituted of a wafer or other material layer, which can in some forms have at least one width dimension exceeding about 2 mm and/or occupy a surface area of at least about 10 mm².

Additional sheet graft embodiments of the invention are provided wherein the features of an embodiment as discussed in the paragraph immediately above are combined with one or more features described in the Detailed Description found below. It is to be understood that the features described in connection with specific embodiments set forth in the Detailed Description are contemplated as being capable of generalization to other embodiments unless clearly indicated otherwise.

Additional embodiments herein relate to methods for preparing one or more depots on a graft material. In certain aspects, such methods comprise depositing on a graft material at least one volume, and in some modes a plurality of volumes, of a flowable material including a drug, and causing the flowable material to harden. In preferred aspects, the sheet graft material includes a porous matrix, and a portion of the flowable material infiltrates the porous matrix, more preferably only partially through the thickness of the sheet graft material. The infiltrated material is hardened during the hardening step, and forms a hybrid matrix with the porous matrix of the sheet material, which can facilitate an attachment of the drug depot to the sheet graft material. Such an attached drug depot can include, in addition to the infiltrated depot material, additional depot material residing outside of the porous matrix, e.g. extending above a surface of the region of the sheet graft material occupied by the depot.

Still further embodiments herein relate to methods for treating a patient, comprising implanting in the patient an implantable sheet graft device as described herein. In certain modes, the sheet graft device is configured to support soft tissue of the patient, and is implanted to as to support soft tissue. In some preferred methods, the sheet graft device is implanted to support tissue adjacent a body wall defect, such as a hernia in an abdominal wall or other location in the patient.

Additional objects, embodiments, forms, features, advantages, aspects, and benefits of the present invention shall become apparent from the detailed description and drawings included herein.

DETAILED DESCRIPTION

Figure 1:
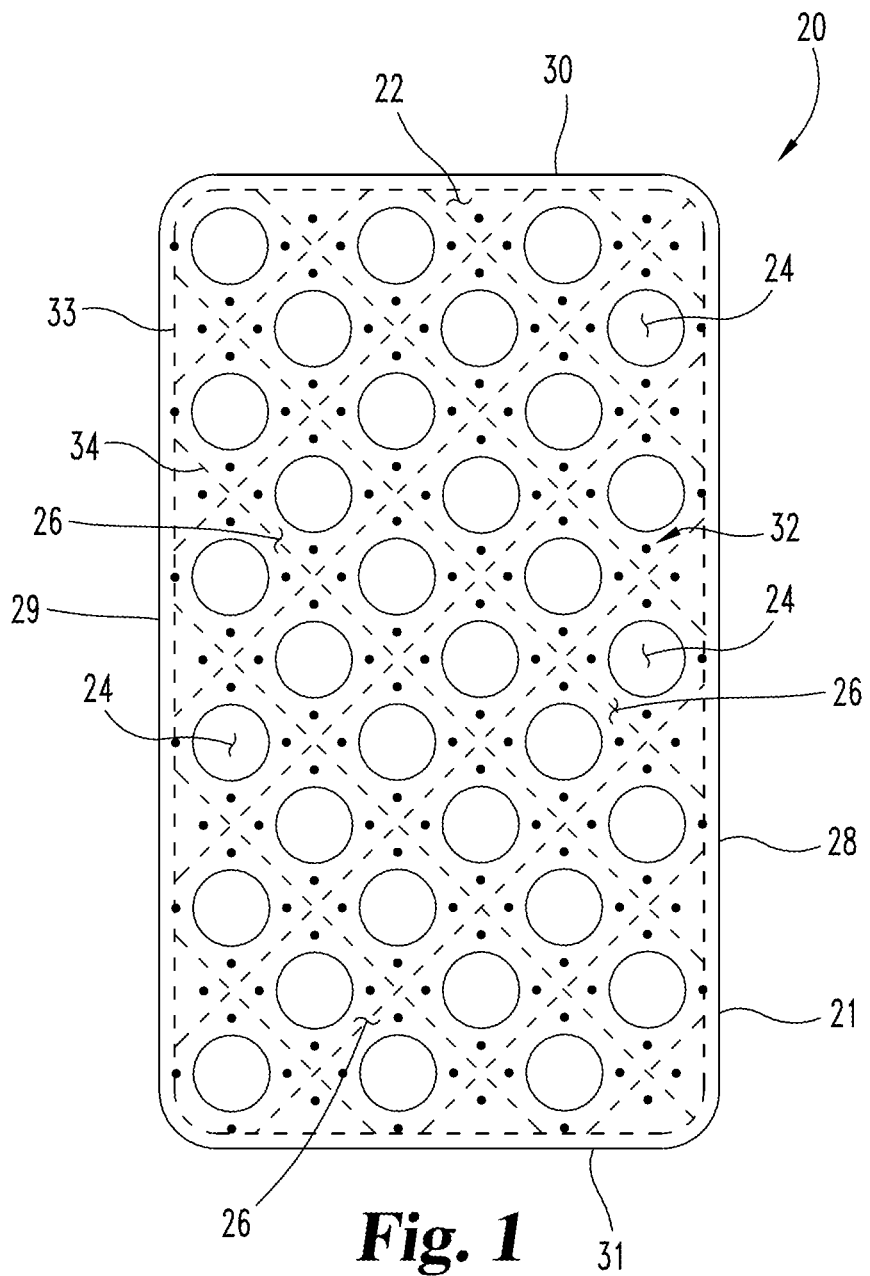
FIG. 1 is a top view of a medical sheet graft device according to one embodiment of the invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, certain aspects of the present invention are directed to graft products that incorporate multiple drug depots in and/or on the products. These products, in some forms, include a sheet graft material, e.g., an absorbable or remodelable sheet material such as extracellular matrix sheet. The sheet graft material can have a plurality of drug depots distributed along an outer surface of the sheet. In certain preferred embodiments, the drug depots are hardened deposits that have been created in situ onto the top and/or bottom side of the sheet, and that can infiltrate at least a portion of the thickness, and preferably only a portion of the thickness, of the sheet. The drug depots incorporate a (at least one) drug and can be capable of eluting the drug. The drug depots are desirably layer bodies or regular or irregular shapes, for example in the form of circular, ovoid or polygonal wafers. Desirably, the drug depots are constructed and arranged to elute the drug over an extended period of time. The depots can be constructed and arranged to elute the drug over a period of time of at least 72 hours, or at least 96 hours, or at least 168 hours, when the device is immersed in an aqueous phosphate buffered saline solution (e.g. as described in Example 1). These same minimum elution times may also be achieved in the target implant site for the graft device, e.g. a subcutaneous implant site or when implanted in a body wall, such as the abdominal wall, to repair damaged tissue such as herniated tissue. Elution can occur for example when bodily fluids contact the drug depots so as to dissolve amounts of the drug, which are then eluted from the depots. When taking the form of hardened deposits, the drug depots can be a dried composition including a bioabsorbable polymeric material and the drug. In some preferred aspects, the drug depots are positioned on the top surface of the sheet graft material, and taken all together occupy less than about 50% of the sheet's top surface, e.g., in some preferred forms occupying at least about 5% but less than about 30% of the top surface. In some forms, the drug depots will be regularly situated, e.g., in a repeating pattern, along the top surface of the sheet. In these and other forms, a plurality of thru-openings such as holes or slits can be made through the sheet graft material in regions which are unoccupied by the drug depots. Such thru-openings can allow fluid to pass through the sheet graft material from one side to the other. As well, other aspects of the present invention provides methods for preparing and using depot-bearing graft constructs, and medical products that include constructs as described herein enclosed within packaging in a sterile condition.

Figure 2:
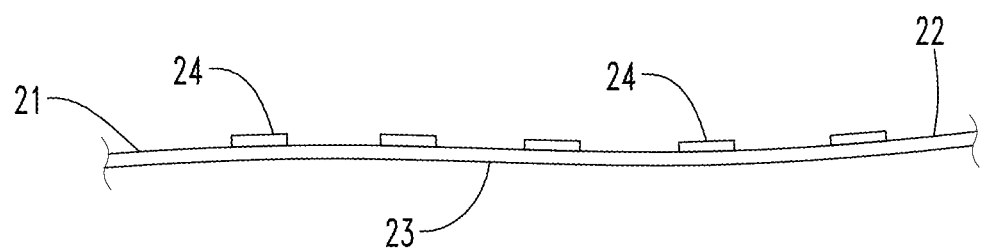
FIG. 2 is a side view of the device of FIG. 1.
Figure 3:
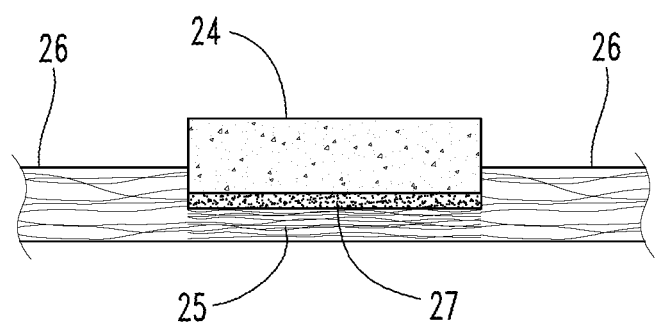
FIG. 3 is an enlarged cross-sectional view of a region of the device of FIGS. 1 and 2 including a drug depot.

With reference now to FIGS. 1 to 3, an inventive sheet graft construct 20 is depicted. Construct 20 includes a sheet graft material 21 having a top surface 22 and a bottom surface 23. Construct 20 also includes a plurality of drug depots 24 attached to corresponding depot-bearing regions 25 of the sheet graft material 21, which are surrounded by depot-free regions 26 of the sheet graft material 21. In the depicted construct 20, a portion of the material of the drug depots 24 is located infiltrated within pores between fibers of a porous fibrous matrix of the sheet graft material 21, forming a hybrid matrix region 27 including fibers of the porous fibrous matrix entrained within material of the drug depots 24. In this fashion, an attachment is created between the drug depots 24 and the sheet graft material 21. Construct 20 as depicted is generally rectangular in shape having a first edge 28 and a corresponding second, opposite edge 29, and a third edge 30 and a corresponding fourth, opposite edge 31. It will be understood that other shapes for the construct will also be suitable within the invention. Construct 20 also includes a plurality of thru-openings 32 in the form of perforations of generally circular cross-section, to allow fluid passage through the construct 20 from one side to the other. As shown, in the preferred device thru-openings 32 are located in depot-free regions of the sheet graft material 21.

Construct 20 also includes a perimeter weaving element 33, such as a suture, extending along the path defined by the outer edges of sheet graft material 21 and spaced inwardly from the edges, for example by a distance of about 0.1 to about 1 cm. Construct 20 also has an interior weaving element or elements 34, such as a suture(s), that provide a pattern of intersecting weave lines, which in the depicted embodiment form generally rectangular (and particularly here square) shapes across the sheet graft material 21. Where sheet graft material 21 is composed of a laminate including multiple layers, weaving elements 33 and 34 can be provided and distributed across the graft material 21 to provide resistance to delamination of the layers. The sutures or other weaving elements 33 and 34 can, for example, provide lock stitches that stitch the layers together for these purposes. A drug depot 24 is located within each rectangular shape provide by weaving element(s) 34.

In certain preferred aspects, the sheet graft material of construct 20 includes multiple ECM layers (e.g., 2 to 10 layers or more), desirably laminated together as described herein, more desirably by dehydrothermal bonding between ECM layers of the laminate, for example using any of the dehydrothermal bonding techniques described herein. The weaving component(s) are desirably bioabsorbable sutures. Additionally, such constructs 20 can incorporate one or more synthetic mesh layers above or below any of the ECM layers as described elsewhere herein, e.g., between any two ECM layers of the laminate or other multiple layer construct.

Generally, the total surface area defined by the top surfaces of the drug depots 24, taken together, will be less than the total surface area of the top surface of the of the sheet graft material 21. In preferred embodiments, the total surface area defined by the top surfaces of the drug depots, taken together, will be less than 50% of the total surface area of the top surface of the of the sheet graft material 24, more preferably less than about 35%, and even more preferably less than about 25%. In certain embodiments, the total surface area defined by the top surfaces of the drug depots, taken together, will be in the range of about 3% to about 50% of the total surface area of the top surface of the of the sheet graft material, more preferably in the range of about 5% to about 35%, and even more preferably in the range of about 8%, to about 25%. Again, when drug depots are associated with a sheet graft material, they can be positioned along the top and/or bottom side of the sheet graft material, and/or embedded within the sheet graft material (e.g. between layers of a laminated construct). Thus, in some embodiments, some of the depots can be located on the top and/or bottom of the sheet material while some are embedded within the sheet graft material, and in other embodiments all of the depots can be on an outer exposed surface of the sheet graft material (i.e. top and/or bottom). Sheet graft embodiments having attached depots in accordance of the invention will thus include depot-free areas or regions between the depots, which can advantageously present the unmodified sheet graft material to the body of a subject when implanted. Where sheet graft materials comprise or are constituted of ECM material or another porous material receptive to cellular invasion, such invasion can occur in the depot-free areas unaffected by the solid depot material.

The total number of drug depots attached to the sheet graft material can vary. It is preferred that at least a substantial proportion of the total dose of drug on the sheet graft device be carried by relatively few drug depots. In some aspects, at least 50%, at least 70%, at least 80%, at least 90%, at least 95%, at least 99%, or all or essentially all of the total dose of the drug on the device, will be incorporated within 2 to about 120 drug depots, preferably about 5 to about 80 drug depots, more preferably about 10 to about 60 drug depots, and even more preferably about 20 to about 50 drug depots. In some embodiments, these numbers of drug depots constitute the total number of drug depots on the device.

The drug depots can be substantially the same size as each other (e.g. having top surfaces that have surface areas within about 20% of one another) or may vary in size, and the drug depots in some embodiments can be completely discrete from one another. It will be understood that while completely discrete depots, unconnected to one another by the same material from which the depots are formed, are preferred, in other forms, the depots might be connected to one another by smaller volumes or masses of the depot material such that the majority of the depot material mass on the device is within the depots (e.g. greater than 80%, or 90% by weight). For example, bands or threads of the depot material may span between more compact or shaped depot wafers or layers as described herein. These embodiments can nonetheless concentrate the drug to be released in the depot regions, while the overall depot material of the device still only occupies a percentage of the surface area of the overall sheet graft device, e.g. those percentages identified above.

At least some (e.g. two or more, five or more, or ten or more) of the above-specified drug depots, or all of the above-specified drug depots, can be material layers that have top surfaces with a surface area of at least about 10 mm$^2$, or at least about 20 mm$^2$, or at least about 50 mm$^2$, and typically in the range of about 10 mm$^2$ to about 1000 mm$^2$, more typically in the range of about 50 mm$^2$ to about 500 mm$^2$. Additionally or alternatively, at least some (e.g. two or more, five or more, or ten or more) of the above-specified drug depots can be material layers with at least one width dimension of at least about 2 mm, more preferably at least about 4 mm, and typically in the range of about 4 mm to about 20 mm; and/or the drug depots can be planar or substantially planar material layers, for example wafers of circular, ovoid, polygonal or other shapes, that when considered in the plane of the material layer have a first, maximum width taken along a first axis which is no more than about three times that a second width taken on an axis perpendicular to and centered upon the first axis. Such characteristics can contribute a preferred, relatively compact shape of the depots.

As an addition or alternative to a consideration of the total number of the above-specified drug depots on the sheet graft construct (which specified drug depots may incorporate either all or a substantial portion of the total dose of drug on the device, as indicated), the percentage of the total dose of the drug on the construct that is incorporated in each of the above-specified drug depots can be a consideration. In certain embodiments, each of the above-specified drug depots incorporates at least about 0.5% of the total dose of drug on the construct, preferably at least about 1%.

The drug depots can be spatially arranged on the sheet graft material in a variety of ways as needed for a particular medical application. The drug depots can be arranged in a regular pattern, for example as shown in FIG. 1, or a random or irregular pattern if desired. Some embodiments will include rows or lines of drug depots. Drug depots may or may not be located across all parts of a surface, e.g., the top side of a sheet graft material. Additionally, drug depots can be distributed on the sheet graft material such that upon implantation, eluted drug from the drug depots diffuses and impregnates the entire sheet graft material. A substantially even distribution of the drug depots across the sheet graft material can be used for these purposes, and/or a porous matrix incorporated into the sheet graft material can facilitate this distribution.

In some embodiments, the maximum thickness of at least some of the drug depots, and potentially all of the depots, will be at least about 25% of the maximum thickness of the sheet graft material, or at least about 100% of the maximum thickness of the sheet graft material, and typically in the range of about 25% to about 500% of the maximum thickness of the sheet graft material. Additionally or alternatively, the average thickness of at least some of the drug depots, and potentially all of the depots, will be at least about 25% of the average thickness of the sheet graft material, or at least about 50% of the average thickness of the sheet graft material, and typically in the range of about 25% to about 500% of the average thickness of the sheet graft material. As well, in certain embodiments, such as that depicted in FIGS. 1 to 3, the drug depots will exposed at the surface of the sheet graft material and will be situated upon a depot-bearing portion of the sheet graft material. In such embodiments, the drug depots can have an average thickness (which includes the thickness of any infiltrated portion of the depots) that is greater than the average thickness of the corresponding depot-bearing portion of the sheet graft material. For example, the drug depots can have an average thickness that is at least 100% of the average thickness of the corresponding depot-bearing portion, and typically in the range of about 100% to 1000% of the average thickness of the corresponding depot-bearing portion. Relatively thick drug depots, for example as specified herein, facilitate the provision of a beneficial extended release of the drug(s) from the depots.

Figure 3A:
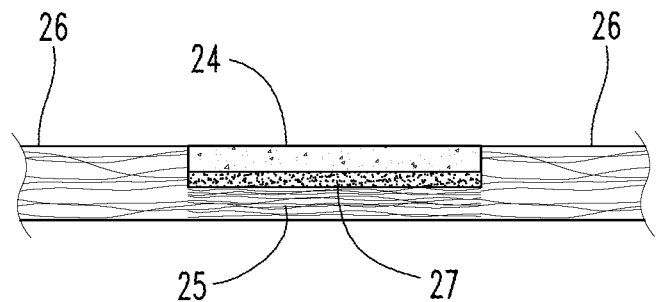
FIG. 3A is an enlarged cross-sectional view of a region of the device of FIGS. 1 and 2 including a drug depot in another embodiment.

FIG. 3A shows another drug depot construct that can be incorporated into the depots of embodiments described herein. The construct of FIG. 3A is similar to that shown in FIG. 3, only having a top surface of the drug depot 24 in plane or at least substantially in plane (e.g. varying by no more than about 2 mm, or no more than about 1 mm, or no more than about 0.5 mm above or below) with the top surface of the sheet graft material 21 adjacent the drug depot 24. This preferred arrangement can in some embodiments provide a substantially smooth top surface to the overall graft device (e.g. device 20).

Figure 4:
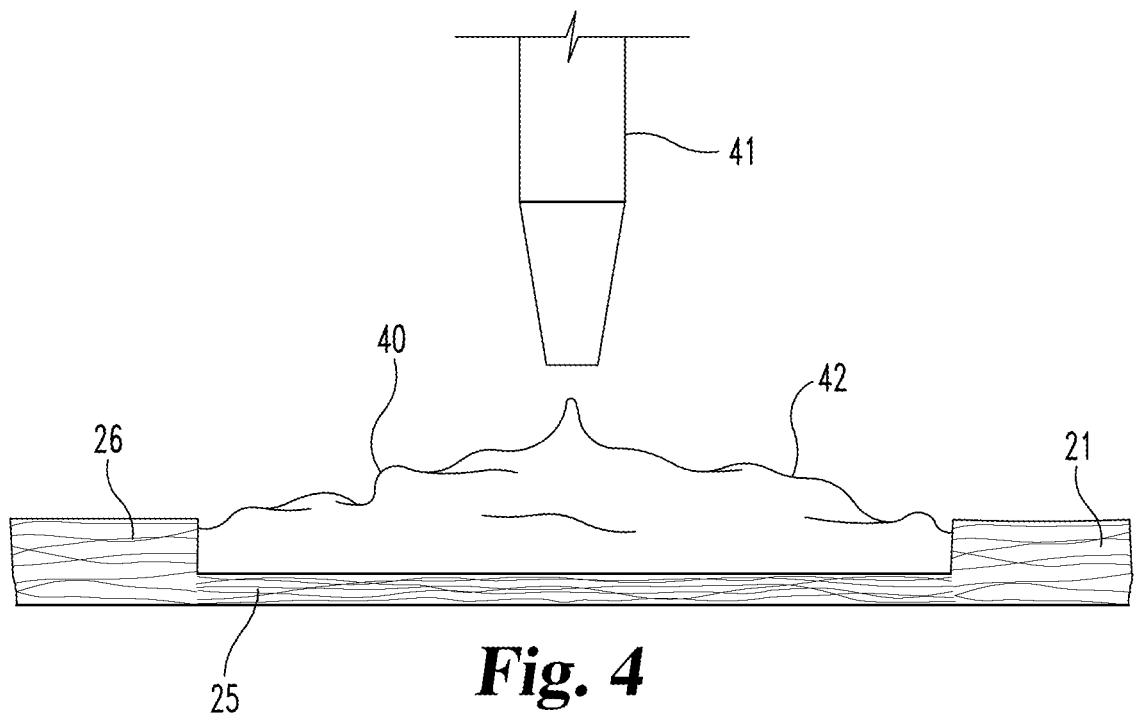
FIG. 4 is a partial side view of a sheet graft device during one stage of its manufacture.
Figure 5:
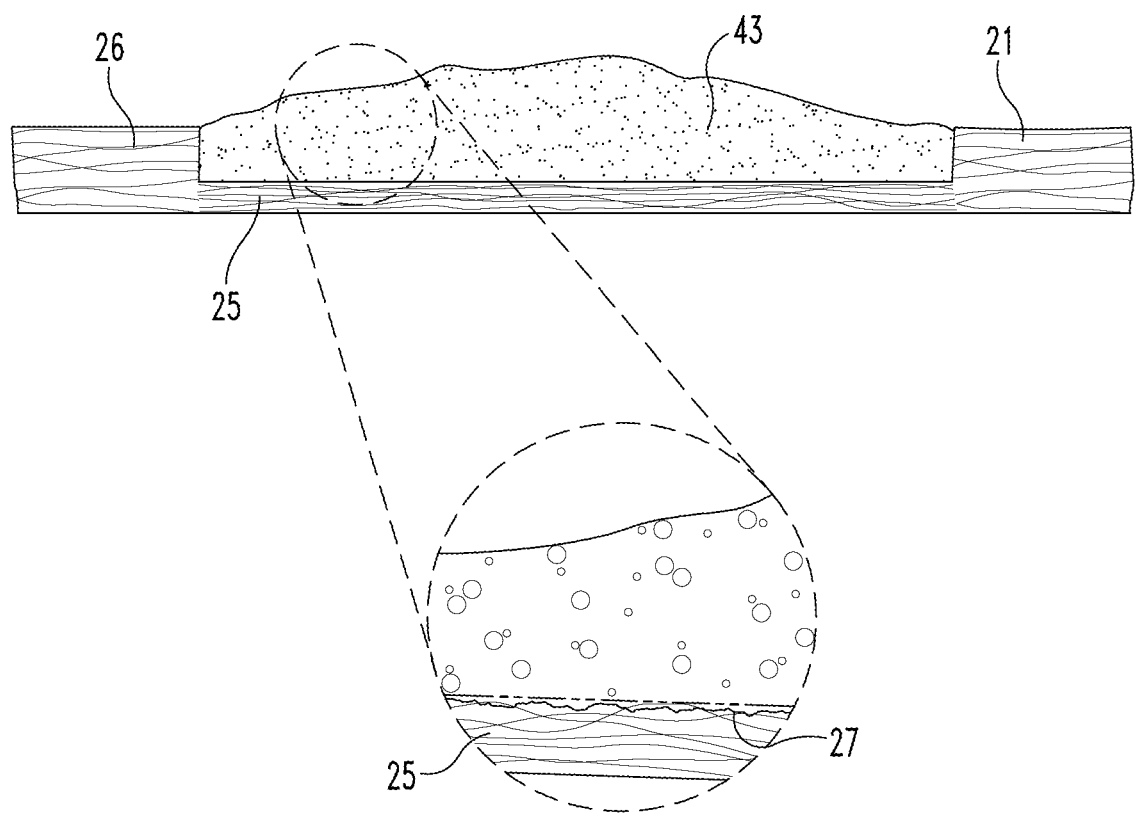
FIG. 5 is a partial, side view of the medical product of FIG. 4 at a subsequent stage of manufacture.

As shown particularly in FIGS. 3 and 3A, when the sheet graft material has a porous matrix, material of the formed drug depot can infiltrate and combine with the porous matrix to form a hybrid matrix. With reference to FIGS. 4 and 5, illustrated is one embodiment of a method by which such a structure can be prepared. As shown in FIG. 4, a flowable material 40 has been ejected from a dispensing nozzle 41 and formed a deposited volume of material 42 supported by the sheet graft material 21. Flowable material 40 incorporates one or more drugs for availability in the implantable product, and typically a carrier material such as a synthetic polymeric material. While still flowable, at least a portion of flowable material 40 infiltrates into a porous matrix of the sheet graft material 21. This can be under pressure caused by the force of gravity, or other means of pressuring the material 40 may also be used, potentially combined with a wicking action of the porous matrix. However, as discussed above, in preferred embodiments the infiltration of the material of the depot is only partially through the thickness of the sheet graft material 21. Control of the level of penetration can be achieved by consideration of various factors including, for example, the viscosity of the deposited flowable material, the extent of porosity of the depot-bearing region of the sheet graft material upon which the flowable material is deposited, the extent of pressure applied to the deposited material, the residence time of the flowable material on the sheet graft material before hardening, and the like. In some modes of practice of the invention, the deposited flowable material can infiltrate into the sheet graft material a distance that equals at least about 1%, or at least about 2%, of the thickness of the corresponding depot-bearing region of the sheet graft material, and typically in the range of about 1% to about 75% of the thickness of the corresponding depot-bearing region of the sheet, preferably in the range of about 1% to about 50%, and more preferably in the range of about 1% to about 20%. As well, as discussed above, in some forms of the invention, the depot-bearing regions of the sheet graft material are denser and/or less porous than adjacent regions of the sheet graft material. This can help to prevent undesired levels of penetration of the deposited flowable material through the sheet graft material.

FIG. 5 shows an illustrative subsequent stage of manufacture where the flowable material has hardened to a non-flowable solid volume 43, a lower portion of which is infiltrated and combined with the porous matrix of sheet 21. The hardening of the flowable material can be caused by any suitable mechanism. In certain embodiments, such hardening is caused at least in part, and potentially completely by, removal of a liquid solvent material from the flowable material, for example by evaporation. This can be accomplished, for example by any suitable drying technique or techniques, including for example drying at atmospheric pressure and/or under vacuum (subatmospheric pressure). Water and/or organic solvent materials may be used for these purposes, with volatile organic solvents, for example acetone, proving beneficial in some methods. In some modes, a polymeric carrier used to form the depot will be soluble in the liquid solvent selected while the drug is not and thus exists in the flowable material as a suspended solid particulate. Further, in some variants, the hardening of the deposited flowable material will cause the formation of entrapped gas bubbles within the hardened volume 43, forming pores therein. Further, in some modes of practice, the manufacture of the depot includes a further step of compressing the non-flowable solid volume 43. This can deform and re-shape the volume 43. For example, this can provide a smoother upper surface to the volume 43 and formed depot, and/or reduce the thickness of the volume 43 and formed depot, and/or where the volume 43 incorporates pores as noted above, can collapse the pores and potentially densify the volume 43 in the formation of the drug depot. As well, during or after such compressing, the volume 43 can be further dried, for example under a vacuum and/or with applied heat, to remove additional amounts of solvent. Such processes can contribute to the desired elution properties of the drug depot.

With continued reference to FIG. 5, while amounts of the drug depot material can infiltrate at least partially into the depot-bearing region of the sheet graft material as discussed above, in preferred embodiments the formed drug depots also include an amount of drug depot material external of and extending beyond the depot-bearing region of the sheet graft material.

While the depot formation can include solvent evaporation or other removal, as noted above, still other methods for forming the depots either in situ on the graft material or separately can be used. For example, these other methods include deposition of molten mixtures which harden upon cooling, heated compression casting of dry powder materials, or other suitable methods.

In certain advantageous embodiments, the sheet graft material will have reservoirs into which the flowable, drug-containing material will be deposited to form the depots. These reservoirs can be formed in the sheet graft material as it is being initially prepared, or can be formed in the sheet graft material after it is prepared, or both, and can have depths of at least about 0.5 mm, or at least about 1 mm. The thus-formed reservoirs can have a bottom wall and sidewalls. In some forms, a sheet graft material having a porous matrix is processed to compress selected regions of the sheet graft material to form these reservoirs. Such compression can densify the sheet graft material underlying and forming the bottom surface of the reservoirs, reducing its porosity. This reduced porosity can in certain embodiments at least partially control the depth of infiltration of a flowable drug-containing material deposited onto the sheet graft material to form a depot, as described elsewhere herein. In one illustrative reservoir-forming process, a mold piece having protrusions corresponding to the reservoirs can be compressed into the porous matrix of the sheet graft material, desirably when the sheet graft material is in a wetted state. With continued compression with the mold piece the sheet graft material can be dried. The reservoirs are thus stably imprinted into the sheet graft material, and remain after the mold or form is removed. Such processing to form reservoirs has been conducted to particular advantage using extracellular matrix sheet graft material as described herein.

After formation of the reservoirs as noted above, depot-forming material can be deposited into the reservoirs. The depot-forming material can at least partially fill the reservoir, and in some embodiments will completely fill the reservoir, potentially with some material provided beyond that necessary to fill the reservoir. The deposited material can contact the bottom wall and sidewalls of the reservoir, which will tend to retain the deposited material in the shape of the reservoir. As well, where the sheet graft material includes a porous matrix, due to infiltration of the depot-forming material into the porous matrix, hybrid matrices including the porous matrix and the depot material can in some embodiments be formed not only in regions adjacent the bottom walls of the reservoirs as discussed above, but also in regions adjacent the sidewalls. After deposit of the depot-forming material in the reservoirs, the depot-forming material can be suitably processed, e.g. as described herein, to form a hardened drug depot.

While products with outwardly exposed drug depots like those shown in FIGS. 1 to 3 are highly useful in certain aspects of the present invention, it will be understood that such products can in other embodiments be incorporated into or provide building blocks for other medical products. For example, a multilayered construct could include multiple drug-eluting depots on any outer surface of the construct and/or embed multiple depots between any two layers of the construct. Illustratively, a product incorporating the construct in FIGS. 1 to 3 could include one or more additional layers, e.g. of a tissue-ingrowth receptive material, over the top side of sheet material 21 and over drug depots 24 so as to cover the bodies. The added layer(s) could then be adhered or otherwise anchored to the drug depots 24 and/or the sheet graft material 21.

Figure 6:
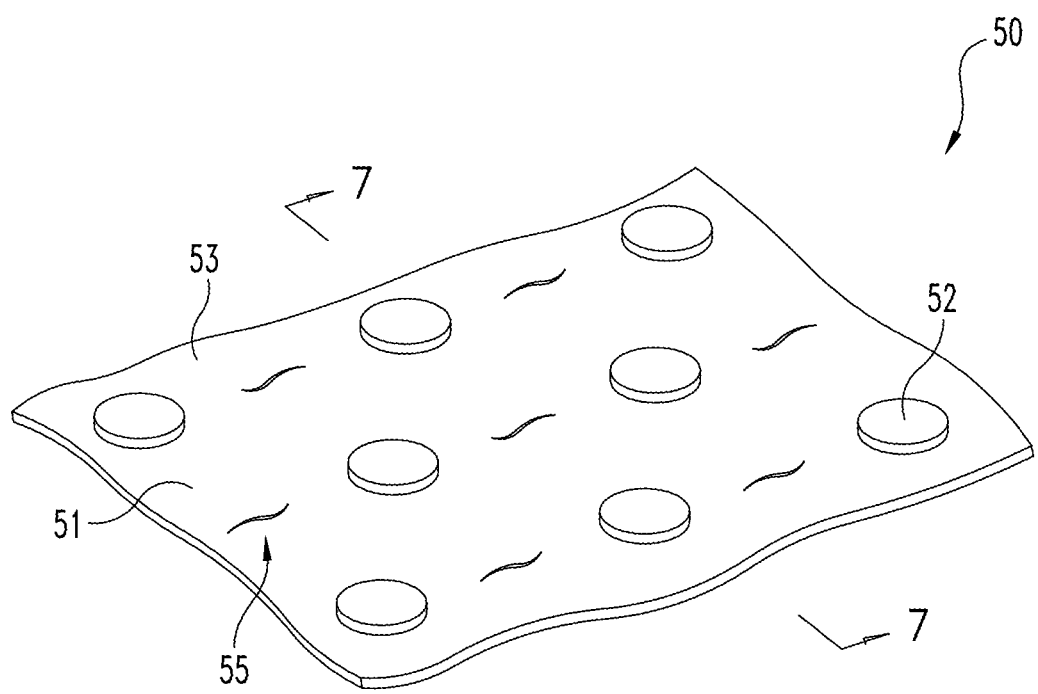
FIG. 6 is a perspective view of a medical product according to one embodiment of the present invention.
Figure 7:
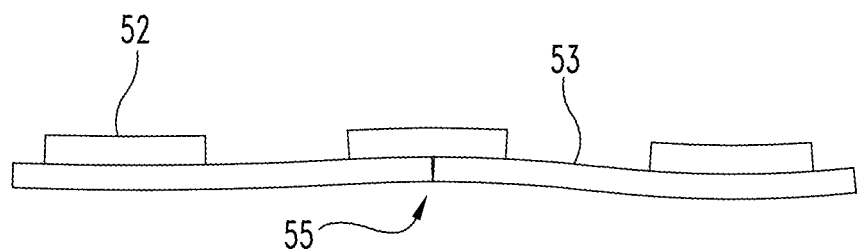
FIG. 7 is a cross-sectional view of the product of FIG. 6 along the view line 7-7 shown in FIG. 6.

While the product of FIGS. 1 to 3 described in relation with FIGS. 4 and 5 is illustrative of embodiments in which drug depots are formed as solid deposits of material onto the sheet graft material, in other embodiments, a drug depot can be created as a separate article and then attached to the sheet graft material. Depots 24 shown in FIGS. 1 to 3 could be separately created and attached to the sheet graft material, to create a sheet graft embodiment herein. As another example, FIGS. 6 and 7 illustrate another sheet graft medical product 50 according to one embodiment of the present invention. This particular product includes a sheet graft material 51 with a plurality of discrete drug depots 52 situated along the sheet's top side 53. Sheet graft material 51 can be made of any suitable material, with materials that are receptive to tissue ingrowth upon implantation in or on the body of a patient being preferred, e.g. those described herein. In some particularly preferred embodiments, the sheet graft material will be or incorporate a remodelable material such as a remodelable extracellular matrix material, including any of those described herein.

With continued reference to FIGS. 6 and 7, drug depots 52, in this illustrative embodiment, are generally disk members with a circular cross-sectional shape, although drug depots can exhibit a variety of shapes and configurations for example, even including bodies that are randomly shaped. The depots can be created separately from the sheet material and then subsequently adhered to or otherwise anchored upon the sheet, for example, with an adhesive, preferably a biodegradable adhesive, which adhesive can itself optionally be drug-loaded. The drug depots can be essentially identical to each other in terms of size, shape, and composition, although this kind of uniformity is certainly not required in all embodiments herein.

Drug depots 52 or other drug depots to be used herein can be formed with one or more biocompatible materials, including for example bioabsorbable and/or non-bioabsorbable materials, and they can be constructed in any suitable manner. Suitable formation techniques include but are not limited to extrusion, hand formation, deposition on a removable backing layer or other substrate, formation in or on a mold or form and/or combinations or variations thereof, just to give a few examples. One or more drugs can be incorporated into such bodies in any suitable manner including, for example, by surface treatment (e.g., spraying, dip coating, etc.) and/or by impregnation (e.g., soaking) of an already-formed body, or in some cases by mixing one or more drugs into a depot-forming material during a manufacturing step, which can thereafter be hardened by drying, curing, crosslinking, polymerization or other means.

Sheet graft device 50 also includes a plurality of slits 55 formed into the sheet, although these slits may be absent in other embodiments. The slits 55 are arranged in a repeating pattern on the sheet graft material 51 and are offset from the drug depots 52, i.e., so as to reside in areas unoccupied by the depots. As discussed herein, in addition to these particular slits, a variety of other slit and non-slit thru-openings can be formed in the sheet graft material.

Figure 8:
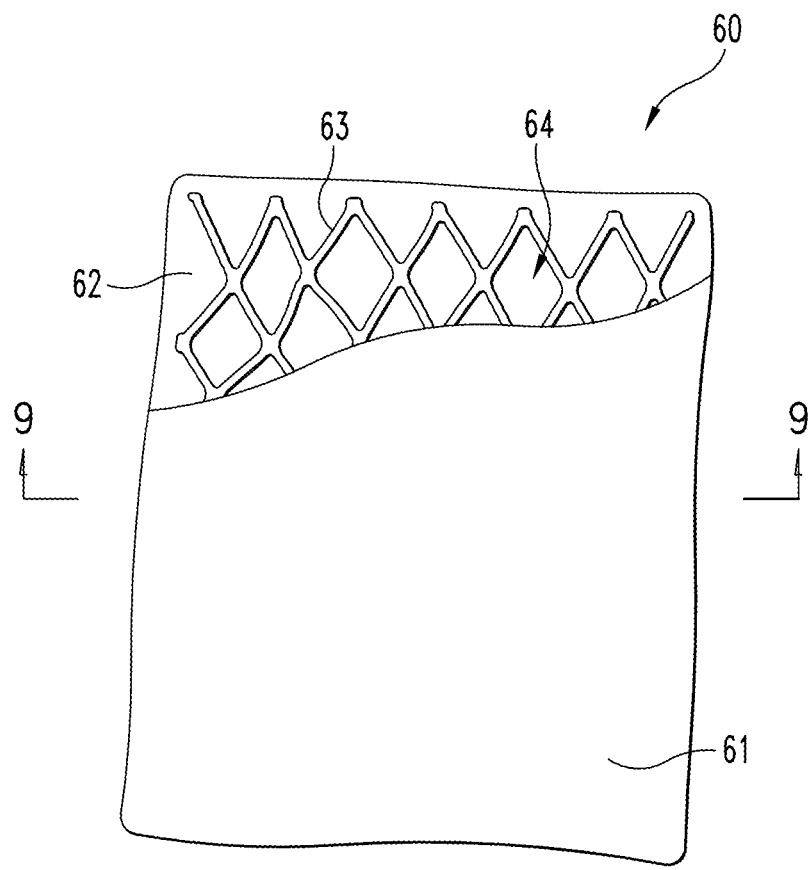
FIG. 8 is a top view of another sheet graft device embodiment.
Figure 9:
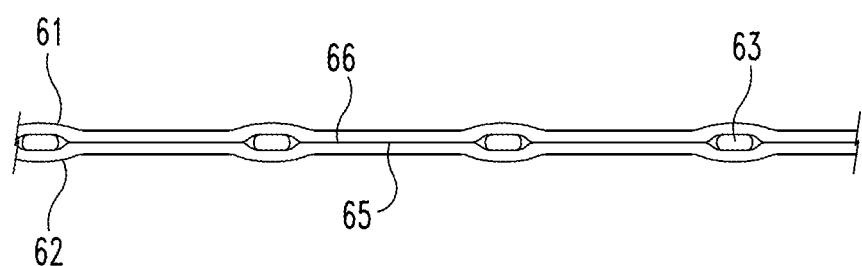
FIG. 9 is a partial cross-sectional view of the product of FIG. 8 along the view line 9-9 shown in FIG. 8.

In some embodiments, a sheet graft material herein will include an extracellular matrix sheet material and a resorbable or non-resorbable synthetic polymer sheet graft material, for example a synthetic polymer mesh or other synthetic polymer layer. FIGS. 8 and 9 illustrate an embodiment combining a synthetic polymer mesh sheet with multiple extracellular matrix layers in accordance with certain aspects of the present invention. Sheet graft construct 60 includes a first sheet 61 and a second sheet 62 of a collagen-containing extracellular matrix material. A portion of the first or top sheet 61 has been cut away in FIG. 8 to reveal a synthetic mesh material 63 (e.g., polypropylene mesh) disposed between the two sheets 60 and 61. The synthetic mesh includes a plurality of mesh openings 64, and as seen in FIG. 9, the top and bottom sheets 61 and 62 contact one another through the plurality of mesh openings 64 so as to provide a corresponding plurality of contacting regions 65 between the apposed faces of sheets 61 and 62.

While not necessary to broader aspects of this embodiment, in this illustrative construction, the top and bottom sheets 61 and 62 are also bonded to one another in regions 65 to provide a plurality of bonded regions 66. By bonding the top and bottom sheets in this manner and around the peripheral edges of the mesh material, the synthetic mesh becomes sealed within the surrounding ECM sheets. Either ECM sheet, top or bottom, might be formed with a single ECM layer or a multilayered ECM construct, for example, a sheet incorporating two, three, four, five, six, seven, eight or more individual ECM layers. Additionally or alternatively, an adhesive (e.g., a drug-loaded adhesive) could be used to bond the top and bottom sheets together through the mesh openings and/or to bond the top and/or bottom sheets directly to the synthetic polymer mesh.

Suitable mesh materials include a large variety of mesh or mesh-like structures. Thus, relative to what is shown in FIG. 8, a suitable mesh can have, among other things, a different number of openings than mesh 63 and/or the shape, size and relative spacing of the openings can be adjusted as desired to suit a particular medical application. Such features can be used to alter the overall percentage of void space in a mesh structure. Illustratively, a mesh opening might be circular, oval, square, rectangular or any other suitable shape.

When incorporated into an inventive graft, a mesh structure, in some embodiments, will be made up of many small filaments, strands or other smaller pieces of material that are interconnected or otherwise associated with one another to form a substantially unitary structure with mesh openings, e.g., like openings 64. When utilized, these smaller pieces may or may not be bonded or directly connected to one another. In alternative forms, a mesh may be or include a material that is manufactured (e.g., by extrusion, in a mold or form, etc.) so as to exhibit essentially a unitary structure. Mesh structures can exhibit a flexibility or compliancy or they can be essentially non-flexible or non-compliant, in whole or in part. Mesh structures can be essentially flat in a relaxed condition, or they can exhibit curvature and/or other non-planar features, for example, exhibiting a convexo-concavo or other three-dimensional shape. A mesh structure, in some aspects, will include multiple layers of material. When a mesh structure is multi-layered, the individual layers may or may not be bonded or otherwise connected to one another. In some embodiments, an inventive graft will incorporate a coated mesh structure (e.g., coated with a composition comprising a drug and a polymeric material, or coated with a drug and subsequently coated with a separate polymer layer, just to give a few examples).

Continuing with FIG. 9, as occurs in contacting regions 65, when opposing collagen-containing surfaces are in contact with one another certain types of advantageous bonding or fusing can occur between those surfaces. While the extent and types of contact between such surfaces can vary, for example, depending on the overall number, sizing and relative spacing of openings in the mesh material, in certain forms, it will be desirable to fuse or bond the surfaces together to form a more interconnected graft body.

In certain embodiments, these contacting collagenous surfaces will desirably be of a character so as to form an attachment to one another by virtue of being dried while compressed against each other. For example, dehydration of these surfaces in forced contact with one another can effectively bond the surfaces to one another, even in the absence of other agents for achieving a bond, although such agents can be used while also taking advantage at least in part on the dehydration-induced bonding. With sufficient compression and dehydration, two collagenous surfaces can be caused to form a generally unitary collagenous structure. Vacuum pressing operations, and the closely bonded nature that they can characteristically impart to the collagen-containing materials, are highly advantageous and preferred in these aspects of the invention. Some particularly useful methods of dehydration bonding ECM materials include lyophilization, e.g. freeze-drying or evaporative cooling conditions.

Drug depots can be incorporated into sheet graft construct 50. For example, such depots can be any of those disclosed herein, e.g., independently formed bodies such as those described in conjunction with FIGS. 6 and 7, and/or drug depots formed in situ on the sheet graft material as described in conjunction with FIGS. 1 to 3 and 4-5. Such drug depots can be placed or formed between the extracellular matrix sheets 61 and 62, potentially in contact with the synthetic mesh material 63, and/or by situating one or more depots along the top and/or bottom surface of the construct 50.

Figure 10:
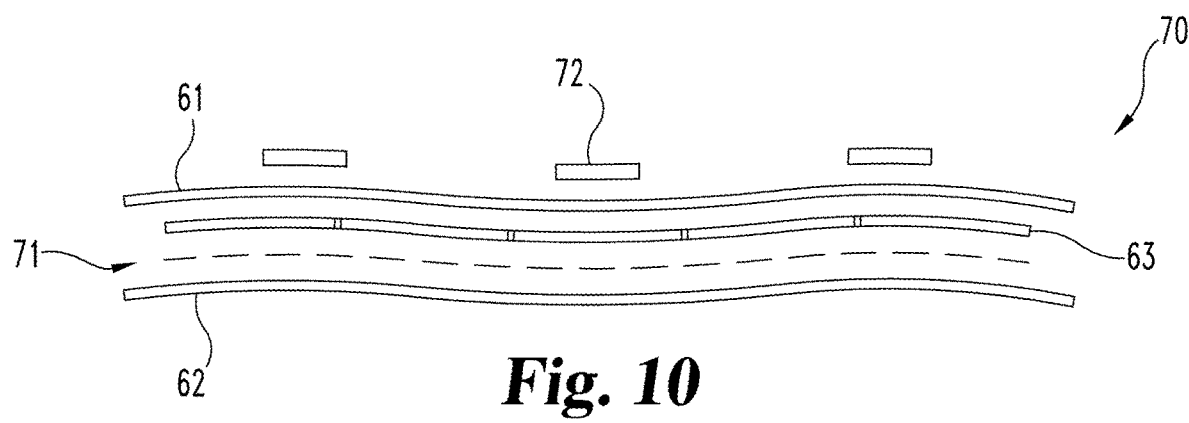
FIG. 10 is an exploded, side view of another sheet graft device embodiment.

Thus, products with sandwiched or embedded meshes like that shown in FIGS. 8 and 9 can be incorporated into or provide components of other medical products of the present invention. Illustratively, FIG. 10 shows an exploded, side view of a medical product 70 according to another embodiment of the invention. A resorbable or non-resorbable synthetic polymer mesh 63 (e.g., a polypropylene mesh) is situated between a first extracellular matrix sheet 61 and a second extracellular matrix sheet 62 with an optional drug-containing adhesive layer 71 occurring between mesh 63 and the second extracellular matrix sheet 62. A plurality of drug depots 72 are situated above the first extracellular matrix sheet 61, i.e., opposite the synthetic polymer mesh 63, so that the depots 72 are not covered by any other sheet or layer and are therefore left exposed to the exterior of the product 70. As noted, the drug depots 72 can be created separately from the sheet material and then subsequently anchored to it, e.g., with a drug-containing or other adhesive, or may be formed in situ on the extracellular matrix sheet 61 as and including the features described herein, either before or after sheet 61 is incorporated into the overall sheet of product 70.

Continuing with FIG. 10, in embodiments where the optional adhesive layer 71 is omitted, dehydration bonding and/or other bonding techniques as discussed elsewhere herein can be used to bond the ECM sheets 61 and 62 together through openings in the polymer mesh 63 and/or to bond the ECM sheets directly to the polymer mesh 63. When an adhesive layer such as layer 71 is present, it can provide some or all of the bonding between the various layers. In respect of the embodiment shown in FIG. 10 and all other embodiments disclosed herein made from multiple constituent pieces, it will be understood that the various pieces can be put together in any suitable order or fashion. In an illustrative method of manufacture for product 70, the polymer mesh and adhesive layer are placed between opposing hydrated ECM layers, and this entire structure is then subjected to compression under dehydration conditions. Subsequently, the drug-eluting bodies are adhered to or formed in situ onto the top surface of the dried hybrid structure. Optionally, product 70 itself can be incorporated into or provide a building block for other medical products of the present invention. For example, in an alternative embodiment, a second synthetic polymer layer (e.g., a resorbable or non-resorbable polymer mesh) can be positioned between the first ECM sheet 61 and the drug depots 72 and/or a third ECM sheet could be positioned over the drug-eluting bodies 72. Optionally, in any of these embodiments, a second group of drug-eluting bodies could be situated below and attached to the second ECM sheet 62.

Figure 11:
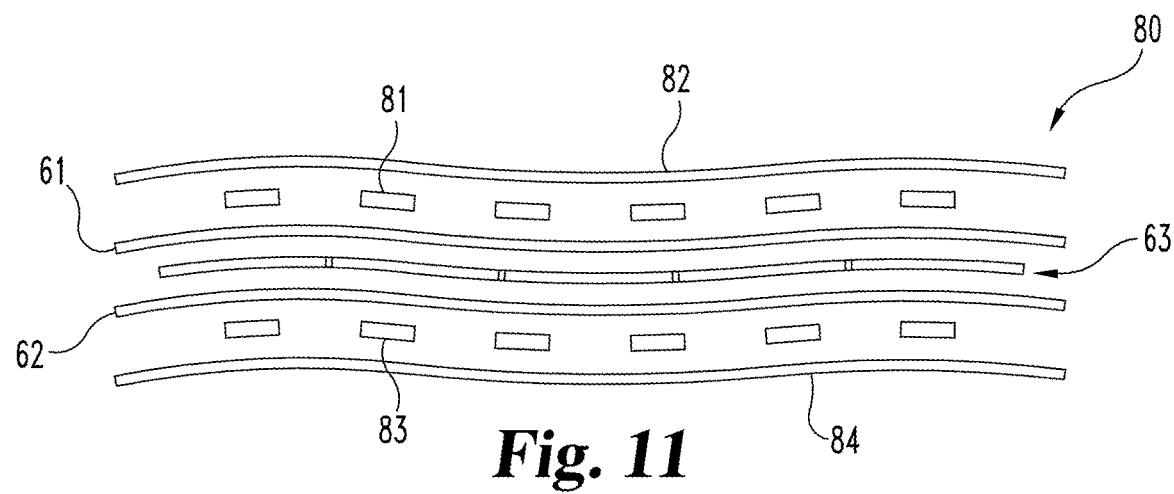
FIG. 11 is an exploded, side view of another sheet graft device embodiment.

FIG. 11 shows an exploded, side view of a sheet graft medical product 80 according to another embodiment of the invention. A synthetic polymer mesh 63 is situated between a first extracellular matrix sheet 61 and a second extracellular matrix sheet 62. Additionally, a first group of drug-eluting bodies 81 is situated between the first extracellular matrix sheet 61 and a third extracellular matrix sheet 82, while a second group of drug-eluting bodies 83 is situated between the second extracellular matrix sheet 62 and a fourth extracellular matrix sheet 84. Again, the various illustrative components can be bonded or otherwise affixed together in any suitable manner including those described herein, and product 80 itself can be incorporated into or provide a component for other medical products of the present invention.

Figure 12:
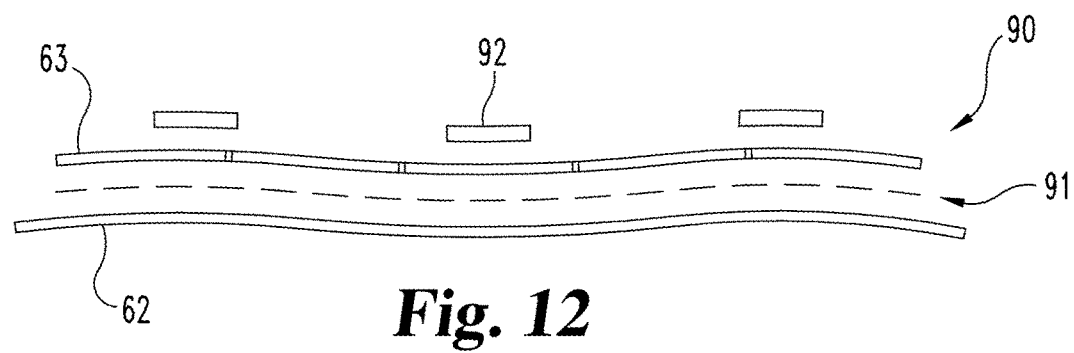
FIG. 12 is an exploded, side view of another sheet graft device embodiment.

FIG. 12 shows an exploded, side view of a medical product 90 according to another embodiment of the invention. A distinct drug-containing adhesive layer 91 is situated between a synthetic polymer mesh 63 and an extracellular matrix sheet 62. Additionally, a plurality of drug-eluting bodies 92 are situated above the synthetic polymer mesh 63, i.e., opposite the extracellular matrix sheet 62, so that the bodies are not covered by any other sheet or layer and are therefore left exposed to the exterior of the product. Optionally, product 90 itself can be incorporated into or provide a building block for many other medical products of the present invention. In an alternative embodiment, a second group of drug-eluting bodies could be situated below the ECM sheet 62 and/or a second ECM sheet could be positioned over the drug-eluting bodies 92.

Figure 13:
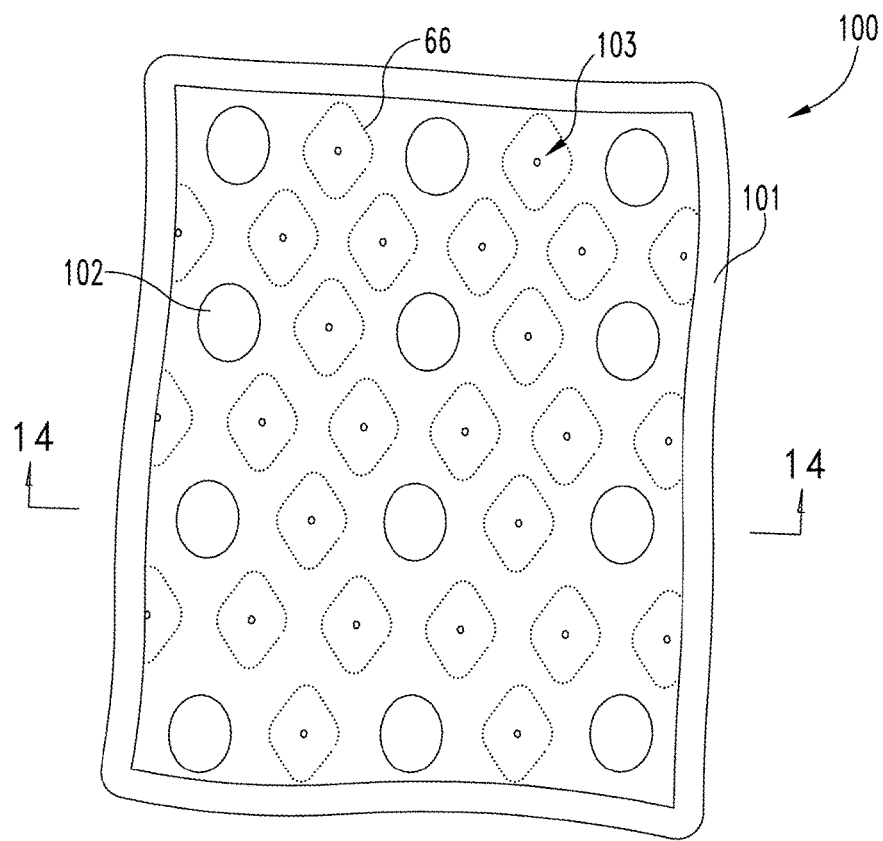
FIG. 13 is a top view of another sheet graft device embodiment.
Figure 14:
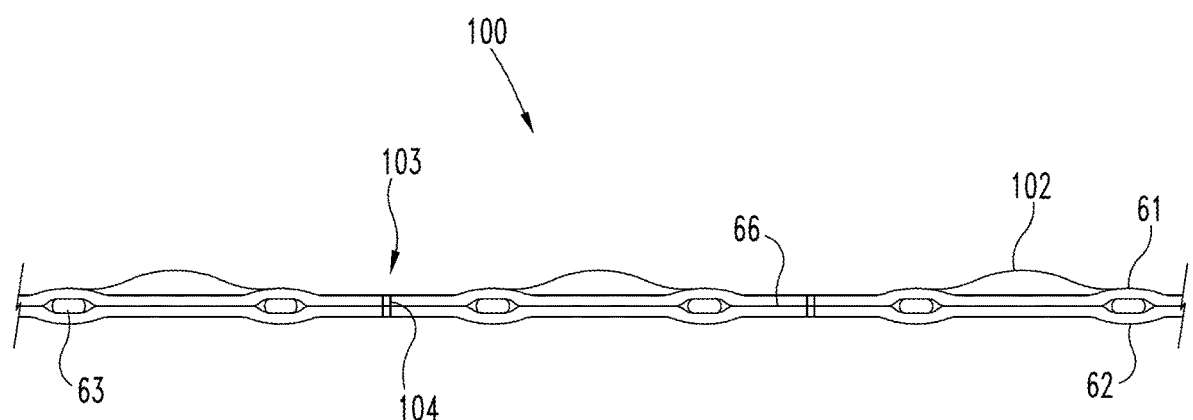
FIG. 14 is a partial, cross-sectional view of the embodiment of FIG. 13 along the view line 14-14 shown in FIG. 13.

FIGS. 13 and 14 depict an illustrative graft construct 100 that incorporates a synthetic mesh material 63, for instance similar to that shown in FIG. 9. In this embodiment, the synthetic mesh 63 is totally encapsulated between and within a top ECM layer 61 and a bottom ECM layer 62. While the actual material of the encapsulated mesh is hidden from view in the completed construct, the contour of the external surface of the construct forms depressions within the openings and protuberances over the mesh elements. This makes it possible to discern the location of the mesh openings, through which the opposing ECM layers have been bonded together to form bonded regions 66. It should be understood however that the shape of a bonded region need not correspond to the shape of an underlying synthetic mesh opening, although this will generally be the case where ECM sheets are pressed in close proximity around a synthetic mesh and bonded together through openings in the mesh. Also, because the synthetic mesh is slightly smaller in area than the ECM sheets, the full bonding together of the opposing ECM layers produces a band 101 of bonded material around the entire periphery of the synthetic mesh. This band is a multilayered bonded ECM region devoid of synthetic mesh material.

A plurality of discrete drug depots 102 have been formed directly onto the top of the graft. While not necessary to broader aspects of the invention, in this embodiment, each depot 102 is positioned over one of the bonded regions 66. Additionally, with this particular design, a single passageway 103 extends through all of the bonded regions except those covered by a depot 102 although passageways could be placed at those locations as well. Passageways 103 include a passageway wall 104 that traverses the entire thickness of the ECM-synthetic mesh combination. As can be seen in FIG. 13, each passageway is generally centered within a corresponding bonded region 66, and the area of the bonded region 66 is considerably larger than the diameter of the passageway 103 such that, when viewed from the top, the bonded region area extends laterally beyond and fully around the passageway. Each generally cylindrical passageway extends through a corresponding opening of the mesh although a 1:1 ratio of passageways to synthetic mesh openings is not required. A particular synthetic mesh opening or bonded region might have two or more passageways associated with it, or it might have none associated with it.

With sufficient bonding between the top and bottom ECM sheets where these sheets meet along the passageway wall 104, the passageway can be substantially isolated from the material of the synthetic mesh 63. This can allow, for example, bodily fluid and other substances to more easily pass from one side of the graft to the other without being able to directly contact the synthetic material 63, or at least not for some period of time following implantation. By using various bonding techniques as discussed herein, the ECM sheets can be bonded together to the point of essentially sealing off the passageway from the synthetic mesh. Additionally, the passageway wall 104 can be lined or coated with a variety of substances, e.g., waxes, oils or absorbable polymers such as PLGA to help further separate or block the passageway from the synthetic mesh 63 if desired.

Figure 15:
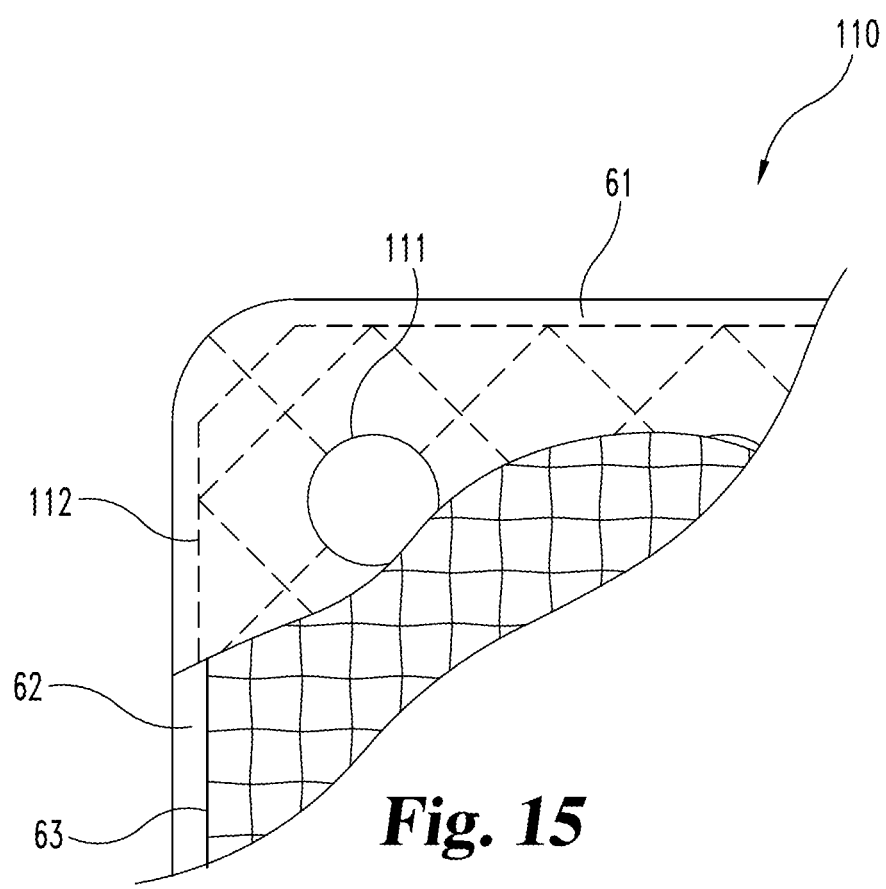
FIG. 15 is a partial cutaway top view of another sheet graft device embodiment.

FIG. 15 depicts an inventive graft construct 110 that incorporates an optional synthetic polymer mesh 63 disposed between a top sheet 61 and bottom sheet 61. The top and bottom sheets 61 and 62 are each constructed of multiple ECM layers, e.g., 2-10 or more individual ECM layers. A drug depot 111 has been formed in situ or otherwise attached onto top sheet 61. A plurality of such drug depots can be attached to the top and/or bottom of the graft constructs in a variety of locations as discussed elsewhere herein. An optional interweaving member 112 (e.g., bioabsorbable suture) affixes the top and bottom sheets together, and in instances where the top and bottom sheets are laminated together, can provide the function of helping to prevent their premature delamination. One or more interweaving members of this sort can be incorporated into any of embodiments disclosed herein. For example, interweaving members such as those illustrated in International Application No. PCT/US2011/063588 (Cook Biotech Incorporated), filed Dec. 6, 2011, which is hereby incorporated by reference in its entirety, can be incorporated into any of the inventive product disclosed herein to provide some level of fixation between any two or more components in the product. Also, as described elsewhere herein, any suitable number and type of slit and non-slit openings can be formed into the product extending fully or partially through any layer of the product.

Continuing with FIG. 15, in one illustrative method of manufacturing this particular embodiment, the synthetic mesh 63 is sandwiched between the top and bottom sheets 61 and 62 (e.g., before any lamination occurs between the top and bottom sheets and/or between the individual ECM layers within each of the top and bottom sheets), and then all of the individual ECM layers are laminated together with the synthetic mesh 63 inside. When included, the interweaving member 112 provides further fixation of the laminated ECM layers. Alternatively, the top and bottom sheets 61 and 62 could be prepared separately by dehydrothermally bonding or otherwise laminating their individual ECM layers together, and when included, the mesh 63 could then be inserted between the previously-prepared sheets. Subsequent bonding of the top and bottom sheets (e.g., with dehydrothermal bonding, use of adhesives and other techniques) and/or installation of one or more interweaving members could then be performed.

In preferred forms, sheet graft materials herein will exhibit a compliancy, particularly when wet, so as to be conformable to tissue structures or regions within a patient to be treated. Sheets graft materials herein can be essentially planar in a relaxed condition, or they can exhibit curvature and/or other non-planar features, for example, exhibiting a curved, convex or other three-dimensional configuration.

A sheet graft material, in some embodiments, will be a laminate made from multiple layers of material, for instance 2 to 20 layers of material, or 2 to 10 layers of material in certain forms. In a laminate sheet, the constituent layers may all be identical, or any one layer may be the same or different than any other layer in terms of its material(s) of construction and/or any other characteristic. Illustratively, suitable laminate structures can include a plurality of ECM layers bonded together, a plurality of non-ECM layers (e.g., biodegradable or non-biodegradable synthetic polymer layers) bonded together, or a combination of one or more ECM layers and one or more non-ECM layers bonded together. Illustratively, two or more ECM sheets can be bonded together using a bonding technique, such as chemical cross-linking or vacuum pressing under dehydrating conditions. An adhesive, glue or other agent may also be used in achieving a bond between material layers. Suitable bonding agents may include, for example, collagen gels or pastes, gelatin, or other agents including reactive monomers or polymers, for example cyanoacrylate adhesives. A combination of one or more of these with dehydration-induced bonding may also be used to bond ECM material layers to one another.

The drug or drugs incorporated in the drug depots can be any of a wide variety of known useful drugs. The drug can be an antimicrobial agent. Illustrative antimicrobial agents include, for example, antibiotics such as penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone, and antiseptics (substances that prevent or arrest the growth or action of microorganisms, generally in a nonspecific fashion) such as silver sulfadiazine, chlorhexidine, sodium hypochlorite, phenols, phenolic compounds, iodophor compounds, quaternary ammonium compounds, and chlorine compounds. Still other drugs can be incorporated in the drug depots, alone or in combination with an antimicrobial agent or each other. Such other drugs may include, for example, anti-clotting agents (e.g. heparin), anti-inflammatory agents, anti-proliferative agents (e.g. taxol derivatives such as paclitaxel), inhibitors of tissue adhesions, nonsteroidal anti-inflammatory drugs (NSAIDs), and others.

Turning now to a more detailed discussion of materials that can be utilized in the present invention, as discussed elsewhere herein, inventive constructs can incorporate naturally derived and/or non-naturally derived materials. In this regard, one or more components of an inventive construct (e.g., a sheet, layer, mesh, drug-eluting depot, just to name a few) may comprise one or more of a variety of synthetic polymeric materials including but not limited to bioresorbable and/or non-bioresorbable plastics. Bioresorbable or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanoates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorable materials may be used, for example, where only a temporary function or presence is desired, and/or in combination with non-bioresorbable materials where only a temporary participation by the bioresorable material is desired. Bioabsorable polymers, such as those identified above, are preferred materials to serve as carriers for drug depots herein, and/or in certain embodiments may also be used to form bioabsorable synthetic polymer meshes used in embodiments herein.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins; polyurethanes; polypropylene; rayon; and rayon-triacetate. In certain embodiments, biostable polymers can be used as carriers in drug depots and/or meshes incorporated in embodiments herein.

As disclosed above, in certain embodiments, the sheet graft material will include a remodelable material. Particular advantage can be provided by devices that incorporate a remodelable material. Such remodelable materials can be provided, for example, by collagenous membrane layer materials isolated from a warm-blooded vertebrate, and especially a mammal. Such isolated collagenous membrane materials can be processed so as to have remodelable, angiogenic properties and promote cellular invasion and ingrowth. Remodelable materials may be used in this context to promote cellular growth on, around, and/or in bodily regions in which inventive devices are implanted or engrafted.

Suitable remodelable materials for incorporation in any of the embodiments herein can be provided by collagenous extracellular matrix (ECM) materials. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. These or other ECM materials can be characterized as membranous tissue layers harvested from a source tissue and decellularized. These membranous tissue layers can have a porous matrix comprised of a network of collagen fibers, wherein the network of collagen fibers retains an inherent network structure from the source tissue. In particular aspects, collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source, and decellularizing the matrix before or after such delaminating. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue, when used in the invention, is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

Submucosa-containing or other remodelable ECM tissue material may retain one or more growth factors native to the source tissue for the tissue material, such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include native heparin, native heparin sulfate, native hyaluronic acid, native fibronectin, native cytokines, and the like. Thus, generally speaking, a submucosa or other ECM material may retain one or more native bioactive components that induce, directly or indirectly, a cellular response such as a change in cell morphology, proliferation, growth, protein or gene expression.

Submucosa-containing or other ECM materials can be derived from any suitable organ or other tissue source, usually sources containing connective tissues.

The ECM materials processed for use in the invention will typically be membranous tissue layers that include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

A submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

In certain forms, inventive devices include a material receptive to tissue ingrowth. Upon deployment of such devices in accordance with the present invention, cells from the patient can infiltrate the material, leading to, for example, new tissue growth on, around, and/or within the device. In some embodiments, the device comprises a remodelable material. In these embodiments, the remodelable material promotes and/or facilitates the formation of new tissue, and is capable of being broken down and replaced by new tissue. Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue. In certain aspects, an extracellular matrix layer or multilayer sheet (e.g. a laminate) includes an open matrix structure formed by lyophilization drying of the layer or sheet.

In certain embodiments, the sheet graft material can include two or more individual layers of ECM material (e.g., 2 or more layers bonded together). The total thickness of such a sheet can be in the range of about 200 microns to about 4,000 microns, e.g., more than about 400 microns, or more than about 600 microns, or more than about 800 microns, or more than about 1,000 microns, or more than about 1,200 microns, or more than about 1,500 microns but typically less than about 2,000 microns. In certain aspects, 2 to about 20 layers of ECM material are bonded in a laminate for use as or in the sheet graft material, more preferably 2 to about 10 layers of ECM material.

The constructs described herein have broad application. In some aspects, inventive products will find use as precursor materials for the later formation of a variety of other medical products, or components thereof. Medical grafts and materials that are already commercially available can be modified in accordance with the present invention as well. In certain embodiments, inventive products are useful in procedures to replace, augment, support, repair, and/or otherwise suitably treat diseased or otherwise damaged or defective patient tissue. Some of the illustrative constructs described herein will be useful, for example, in treating body wall defects such as herniated tissue in an abdominal or other body wall, although inventive constructs and materials can be developed and used in many other medical contexts. In this regard, when used as a medical graft, inventive constructs can be utilized in any procedure where the application of the graft to a bodily structure provides benefit to the patient.

The present invention also provides, in certain aspects, medical products that include a graft construct as described herein in a sealed medical package. In some forms of the invention, such medical products include the graft construct enclosed in sterile condition within medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly. The medical packaging in other aspects can include a further, outer package containing a dessicant, which can act to maintain a dry condition of the construct within the inner package when that inner package is somewhat vapor permeable.

In order to promote a further understanding of aspects of the present invention and features and advantages thereof, the following specific Examples are provided. It will be understood that these Examples are illustrative, and not limiting, of the invention.

EXAMPLE 1

Preparation of Distributed Depot ECM Construct

A. Preparation of ECM Laminate with Reservoirs

An 8-ply layered lyophilized SIS sheet was prepared. The sheet had approximately 12 mm diameter circular craters with raised walls, formed by an embossing mold compressed against the 8 SIS layer plies during lyophilization under conditions to bond the layer plies to one another dehydrothermally. Each crater is formed to have a diameter of 12 mm-13 mm with depth from bottom of the crater to the top of the surrounding wall of about 1 to 2 mm. The ECM material underlying the craters is denser and less porous than the ECM material in surrounding regions due to the compression of the material underlying the craters during drying. The formed SIS laminate sheet is perforated (1.5 mm diameter open perforations) and quilted with a 6-0 bioabsorbable polyglycolic acid (PGA) thread, with a 4 mm quilt spacing in a pattern generally as shown in FIG. 1, and cut to size with an appropriate templates or die.

B. In-situ Formation of Depot Deposits

A 20% w/v solution of poly-DL-Lactide-Co-Glycolide (PLGA) (50:50 PL:GA) in acetone is prepared and 15.68% w/w gentamicin sulfate powder (equivalent to 10.232% w/w gentamicin freebase) to the total solids (PLGA+gentamicin sulfate powder) is suspended in the acetone solution. A controlled volume of the solution was deposited into each crater on the SIS laminate sheet at a volume of 240 μL per crater to form each depot. The depots are dried on the SIS laminate sheet in a two stage process. The deposited material was first dried using air drying at room temperature, forming solidified depot material entraining air bubbles. In a second drying step, the deposited material was further dried by clamping the sheet between two porous inert polymeric sheets and drying the clamped construct in a vacuum oven under vacuum and heat (70° C.) for 4 days. The clamping and drying process compressed the depot material, collapsing the air bubbles and reducing the thickness of the depots.

EXAMPLE 2

Gentamycin Depot Elution Testing

A. Collection of Test Articles

For this study, since it was difficult to implant multiple of the whole 13×22 cm devices prepared as in Example 1 with 33 depots (as shown in FIG. 1) each into the peritoneal cavity of a young 45 Kg domestic pig, the depot regions of the SIS laminate sheet were cut out with a 15 mm diameter die. All such depot/ECM samples were collected from prepared 6-7 laminate sheet devices and pooled to randomize. These were the test articles. The test articles were packaged in small groups, labeled and ETO sterilized.

B. In Vitro Elution Study

An in vitro elution test was carried out by soaking each test article in 5 mL of phosphate buffered saline (PBS) solution (66.7 mM phosphate buffer prepared by dissolving 1.65 g potassium phosphate monobasic and 14.63 g sodium phosphate dibasic heptahydrate in 1000 mL of water) at 37° C. for a specified time period. Then the same test article was moved into a fresh vial of PBS and soaked at 37° C. for the next duration of time point while maintaining traceability throughout. The soak solutions thus collected were assayed for content of USP gentamicins using known procedures, by colorimetric treatment followed by HPLC and UV detection. The 3-4 major peaks representing the gentamicin were integrated to estimate the total gentamicin present in the solution. A five point calibration from 10 mcg/mL to 500 mcg/mL was run with every batch made from the same lot of gentamicin from vendor used to manufacture the devices. An elution profile graph thus obtained is presented in FIG. 16.

C. In Vivo Elution Study

An in vivo elution study was conducted by implanting test articles collected as described above intraperitoneally in a pig. Test articles were implanted in the intraperitoneal abdominal space of a domestic swine such that the total dose of gentamicin freebase present in the implants was equal to or greater than 1.5 times the highest documented intra venous dose of 7 mg/kg body weight in a once-daily injection regime. The serum gentamicin levels were tested at 0 (just pre-implant), 4 hr, 24 hr, 48 hr, 72 hr, 120 hr, 290 hr post implant using a validated LCMS assay.

Gross necropsy was conducted after 290 hours time point and what was left of the implants was observed and collected. Un-implanted test articles from the same lot were tested by using the above-noted colorimetric USP content of gentamicin assay by HPLC/UV for determining average gentamicin content and in vitro elution profile. Some of the explanted test articles were also tested for average gentamicin content left after 290 hours in vivo. Similar content of gentamicin present in the un-implanted depots vs. the explanted test articles was carried out using liquid chromatography-mass spectrometry (LCMS).

More specifically, the test articles un-implanted were soaked in vials containing high purity water (HPW) at the rate of 5 mL per article. The explanted test articles obtained were separated if adhered to one another, rinsed quickly with 2-3 mL of HPW by dropper to remove any gentamicin already eluted and any excess blood present. The explanted samples were then placed in vials containing HPW at 5 mL per article.

Vials containing test articles were closed and incubated at 80° C. with 200 rpm orbital shaking for 46 hours to extract most of the gentamicin entrapped in the PLGA by degrading the polymer via accelerated hydrolysis. After cooling, the exhaustive extraction solutions were assayed for content of gentamicin as described above. An assessment of the data from these studies showed that each test article was originally loaded with 4.522±0.306 mg gentamicin freebase. Based on the number of test articles implanted (110) in the pig the total dose of gentamicin implanted was 497.42 33.66 mg gentamicin freebase. This was estimated as a dose of 11.05±0.75 mg/Kg bw of the pig, which is approximately 1.6 time greater than the maximum dose of gentamycin given once-daily intravenously to humans.

The measured serum levels of gentamycin in the pig are shown in FIG. 17. Also, based on an analysis of 12 randomly selected un-implanted test articles and 12 randomly-selected explanted test articles, an estimated 16% of the gentamycin originally present remained in the explanted test articles (after 290 hours of implantation in vivo).

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. An implantable device, comprising:
   a sheet graft material having a top side and a bottom side;
   a plurality of drug depots attached to the sheet graft material;
   wherein the sheet graft material has a porous matrix formed by a network of fibers, the porous matrix having pores formed between the fibers of the network;
   wherein the drug depots each comprise solid deposits including a polymeric carrier and at least one drug, the solid deposits each including a first portion infiltrating pores of the porous matrix and a second portion external of the porous matrix;
   wherein the sheet graft material has a thickness extending between the top surface and the bottom surface;
   wherein the first portions of the drug depots extend only partially through the thickness of the sheet graft material;
   wherein each said drug depot covers a corresponding depot-bearing portion of the sheet graft material;
   wherein each said depot-bearing portion of the sheet graft material is thinner than depot-free portions of the sheet graft material occurring between the depot-bearing portions;
   wherein each said depot-bearing portion of the sheet graft material is denser than the depot-free portions of the sheet graft material occurring between the depot-bearing portions;
   wherein the drug depots include 5 or more drug depots each having a top surface with a surface area of about 50 mm$^2$ to about 500 mm$^2$;
   wherein the first portions of the drug depots and the fibers form a hybrid matrix region including fibers entrained within the matrix of the first portions of the drug depots.

2. The implantable device of claim 1, wherein the sheet graft material comprises an extracellular matrix sheet material.

3. The implantable device of claim 1, wherein the drug is an antibiotic agent.

4. The implantable device of claim 1, wherein the drug is gentamycin.

5. The implantable device of claim 1, wherein the depots are capable of eluting the drug over a period of time greater than about 72 hours when the device is immersed in 66.7 mM phosphate buffered saline at 37° C.

6. The implantable device of claim 1, wherein the depots are attached to the top side of the sheet graft material, and wherein the depots in combination cover less than about 50% of the surface area of the top side of the sheet material.

7. The implantable device of claim 1, having from 5 to about 80 of said drug depots attached to the sheet graft.

8. The implantable device of claim 1, wherein:
   each depot-bearing portion has a surface area constituting about 0.5% to about 15% of the surface area of the top surface of the sheet graft material.

9. The implantable device of claim 1, wherein:
   the 5 or more drug depots each having a top surface with a surface area of about 50 mm$^2$ to about 500 mm$^2$ are in the form of wafers having a circular, ovoid, or polygonal shape.

10. The implantable device of claim 1, wherein:
    each said depot-bearing portion of the sheet graft material is selectively compressed and thereby less porous and denser than depot-free portions of the sheet graft material occurring between the depot-bearing portions.

11. The implantable device of claim 1, wherein:
    the drug depots are formed by a process including:
    depositing a flowable material including a carrier polymer and the at least one drug onto the top side of the sheet graft material so as to form a plurality of deposited material portions; and
    hardening the deposited material portions.

12. The implantable device of claim 1, wherein:
    the sheet graft material comprises one or more membranous tissue layers harvested from a source tissue of a warm-blooded vertebrate animal and decellularized, and wherein the network of fibers comprises a network of collagen fibers that retains an inherent network structure from the source tissue.

13. The implantable device of claim 12, wherein the one or more membranous tissue layers is effective when implanted in a subject to become infiltrated with cells of the subject.

14. The implantable device of claim 12, wherein the one or more membranous tissue layers is effective when implanted in a subject to become replaced by tissue of the subject.

15. An implantable device, comprising:
a graft material having a porous matrix formed by a network of fibers, the porous matrix having pores formed between the fibers of the network;
a plurality of drug depots including a polymeric carrier and a drug, the drug depots including a first portion infiltrating pores of the porous matrix and a second portion external of the porous matrix, wherein the first portion extends only partially through a thickness of the porous matrix, and wherein the first portion and fibers of the network of fibers form a hybrid matrix region including fibers entrained within material of the first portion;
wherein the drug depots include 5 or more drug depots each having a top surface with a surface area of at least 50 mm$^2$; and
wherein the depots are capable of eluting the drug over a period of time greater than about 72 hours when the device is immersed in 66.7 mM phosphate buffered saline at 37° C.

16. The implantable device of claim 15, wherein the graft material comprises an extracellular matrix material.

17. The implantable device of claim 15, wherein the drug is an antibiotic agent.

18. The implantable device of any one of claim 17, wherein the drug is gentamycin.

19. The implantable device of claim 15, wherein from 5 to about 80 of said drug depots incorporate at least 80% of a total dose of the drug on the device.

20. An implantable device, comprising:
a sheet graft material having a top side and a bottom side;
a plurality of drug depots attached to the sheet graft material, the drug depots including a polymeric carrier and a drug; and
wherein from 5 to 80 of said drug depots incorporate at least 80% of a total dose of the drug on the device;
wherein 5 or more of the drug depots each have a top surface with a surface area of at least 50 mm$^2$;
wherein, the sheet graft material has a porous matrix formed by a network of fibers, the porous matrix having pores formed between the fibers of the network;
the drug depots comprise solid deposits including a first portion infiltrating pores of the porous matrix and a second portion external of the porous matrix;
wherein the first portions of the drug depots and the fibers form a hybrid matrix region including fibers entrained within the matrix of the first portions of the drug depots.

21. The implantable device of claim 20, wherein:
the first portions of the drug depots extend only partially through the thickness of the sheet graft material.

22. The implantable device at claim 20, wherein the drug is gentamycin.

* * * * *